US006900187B2

(12) United States Patent
Gleave et al.

(10) Patent No.: US 6,900,187 B2
(45) Date of Patent: May 31, 2005

(54) TRPM-2 ANTISENSE THERAPY USING AN OLIGONUCLEOTIDE HAVING 2'-O-(2-METHOXY)ETHYL MODIFICATIONS

(75) Inventors: Martin Gleave, Vancouver (CA); Paul S. Rennie, Richmond (CA); Hideaki Miyake, Vancouver (CA); Colleen Nelson, Surrey (CA); Brett P. Monia, Encinitas, CA (US)

(73) Assignee: The University of British Columbia, Vancouver (CA)

(*) Notice: Subject to any disclaimer, the term of this patent is extended or adjusted under 35 U.S.C. 154(b) by 600 days.

(21) Appl. No.: 10/080,794

(22) Filed: Feb. 22, 2002

(65) Prior Publication Data

US 2003/0166591 A1 Sep. 4, 2003

Related U.S. Application Data

(63) Continuation-in-part of application No. 09/944,326, filed on Aug. 30, 2001, and a continuation-in-part of application No. 09/913,325, filed as application No. PCT/US00/04875 on Feb. 25, 2000.
(60) Provisional application No. 60/121,726, filed on Feb. 26, 1999.

(51) Int. Cl.[7] .............................................. A61K 31/70

(52) U.S. Cl. ....................................................... 514/44

(58) Field of Search ........................... 435/6, 91.1, 325; 536/24.3, 24.5, 24.33; 514/44

(56) References Cited

U.S. PATENT DOCUMENTS

| 5,789,389 A | 8/1998 | Tarasewicz et al. |
| 6,172,216 B1 | 1/2001 | Bennett et al. |
| 6,335,194 B1 | 1/2002 | Bennett et al. |
| 6,383,808 B1 | 5/2002 | Monia et al. ............... 435/375 |

FOREIGN PATENT DOCUMENTS

| WO | WO 00/49937 A2 | 8/2000 |
| WO | WO 01/46455 A2 | 6/2001 |
| WO | WO 02/22835 A1 | 3/2002 |
| WO | WO 03/062421 A1 | 7/2003 |
| WO | WO 03/072591 A1 | 9/2003 |

OTHER PUBLICATIONS

Buttyan et al., "Induction of the TRPM–2 Gene in Cells Undergoing Programmed Death" *Molecular and Cellular Biology* Aug. 1989, vol. 9, No. 8, pp. 3473–3481.
Miller et al., "Localization of mRNAs by in–situ hybridization to the residual body at stages IX–X of the cycle of the rat seminiferous epithelium: fact or artefact?" *International Journal of Andrology*, 17:149–160.
Darby et al., "Vascular Expression of Clusterin in Experimental Cyclosporine Nephrotoxicity" *Exp Nephrol* 1995; 3:234–239.
Milner et al., "Selecting effective antisense reagents on combinatorial oligonucleotide arrays" *Nature Biotechnology* vol. 15, Jun. 1997, pp. 537–541.
Sensibar et al., "Prevention of Cell Death Induced by Tumor Necrosis Factor alpha in LNCaP Cells by Overexpression of Sulfated Glycoprotein–2 (Clusterin)," *Cancer Research*, Jun. 1, 1995, vol. 55, pp. 2431–2437.

(Continued)

*Primary Examiner*—Jeffrey Fredman
*Assistant Examiner*—Heather G. Calamita
(74) *Attorney, Agent, or Firm*—Oppedahl & Larson LLP

(57) ABSTRACT

A compound consisting of an oligonucleotide of sequence CAGCAGCAGAGTCTTCATCAT, where the oligonucleotide has a phosphorothioate backbone throughout, the sugar moieties of nucleotides 1–4 and 18–21 bear 2'-O-methoxyethyl modifications, and the remaining nucleotides (nucleotides 5–17) are 2'-deoxynucleotides, and where the cytosines of nucleotides 1, 4 and 19 are 5-methylcytosines. The compound has increased stability in vivo and improved in vitro and in vivo antitumor activity.

11 Claims, 10 Drawing Sheets

OTHER PUBLICATIONS

Miyake et al., "Testosterone–repressed Prostate Message–2 Is an Antiapoptotic Gene Involved in Progression to Androgen Independence in Prostate Cancer", *Cancer Research 60*, Jan. 1, 2000, pp. 170–176.

Yang et al., "Nuclear clusterin/XIP8, an x–ray–induced Ku70–binding protein that signals cell death", *Proc. Nat'l. Acad. Sci. USA*, vol. 97, Issue 11, pp 5907–5912, May 23, 2000.

Benner, et al., "Combination of Antisense Oligonucleotide and Low–Dose Chemotherapy in Hematological Malignancies", *Journal of Pharmacological and Toxicological Method*, 37:229–235 (1997).

Kadomatsu, et al, "Expression of sulfated glycoprotein 2 is associated with carcinogenesis induced by N–nitroso–N–methylurea in rat prostate and seminal vesicle", *Cancer Res* Apr. 1, 1993, 53(7):1480–1483.

Kyprianou, et al., "bcl–2 over–expression delays radiation–induced apoptosis without affecting the clonogenic survival of human prostate cancer cells.", *Int J Cancer*, Jan. 27, 1997, 70(3):341–348.

Wright, et al., "A ribonucleotide reductase inhibitor, MDL 101,731, induces apoptosis and elevates TRPM–2 mRNA levels in human prostate tumor xenografts.", *Exp Cell Res*, Jan. 10, 1996, 222(1):54–60.

Bruchovsky, et al., "Control of tumor progression by maintenance of apoptosis.", *Prostate Suppl.*, 1996, 6:13–21.

Gleave et al., Use of Antisense Oligonucleotides Targeting the Antiapoptotic Gene, Clusterin/Testosterone–Repressed Prostate Message 2, To Enhance Androgen Sensitivity and Chemosensitivity in Prostate Cancer, Urology, 2001, pp. 39–49, vol. 58.

Gleave et al., Antisense therapy: Current status in prostate cancer and other malignancies, Cancer and Metastasis Reviews, pp. 79–92, vol. 21.

Gleave et al., Targeting anti–apoptotic genes upregulated by androgen withdrawal using antisense oligonucleotides to enhance androgen–and chemo–sensitivity in prostate cancer, Investigational New Drugs, 2002, pp. 145–158, vol. 20, No. 2, XP 009021411.

Gleave et al., Antisense Targets to Enhance Hormone and Cytotoxic Therapies in Advanced Prostate Cancer, Current Drug Targets, pp. 209–221, vol. 4.

Jones et al., Molecules in focus. Clusterin, The International Journal of Biochemistry & Cell Biology, 2002, pp. 427–431, vol. 34, XP002262319.

Miyake et al., Antisense TRPM–2 Oligonucleotides Chemosensitize Human Androgen–Independent PC–3 Prostate Cancer Cells Both in Vitro and in Vivo[1], Clinical Cancer Research, May 1, 2000, pp. 1655–1663, vol. 6.

Miyake et al., Testosterone–repressed Prostate Message–2 Is an Antiapoptotic Gene Involved In Progression to Androgen Independence in.Prostate Cancer[1], Cancer Research, Jan. 1, 2000, pp. 170–176, vol. 60.

Miyake et al., Synergistic Chemsensitization and Inhibition of Tumor Growth and Metastasis by the Antisense Oligodeoxynucleotide Targeting Clusterin Gene in a Human Bladder Cancer Model[1], Clinical Cancer Research, pp 4245–4252, vol. 7.

Miyake et al., Novel therapeutic strategy for advanced prostate cancer using antisense oligodeoxynucleotides targeting antiapoptotic genes upregulated after androgen withdrawal to delay androgen–independent progression and enhance chemosensitivity, International Journal of Urology,, pp. 337–349, vol. 8, No. 7.

Rosenberg et al., Cluster: Physiologic and Pathophysiologic Considerations, International Journal of Biochemistry Cell Biology, pp. 633–645, vol. 27, No. 7.

Wilson et al., Clusterin is a secreted mammalian chaperone, Trends in Biological Sciences, Mar. 1, 2000, pp 95–98, vol. 25, No. 3, XP004202536.

Wong et al., Molecular characterization of human TRPM–2/ clusterin, a gene associated with sperm maturation, apoptosis and neurodegeneration, European Journal of Biochemistry, pp. 917–925, vol. 227, No. 3, XP 001146404.

Zangemeister–Wittke et al., A Novel Bispecific Antisense Oligonucleotide Inhibiting Both bcl–2 and bcl–xL Expression Efficiently Induces Apoptosis in Tumor Cells[1], Clinical Cancer Research, Jun. 1, 2000, pp. 2547–2555, vol. 6.

Zellweger et al., Antitumor Activity of Antisense Clusterin Oligonucleotides is Improved in Vitro and in Vivo by Incorporation of 2'–O–(2–Methoxy)Ethyl Chemistry, The Journal of Pharmacology and Experimental, May 11, 2001, pp. 934–940, vol. 298, No. 3.

Zellweger et al., Chemosensitization of Human Renal Cell Cancer Using Antisense Oligonucleotides Targeting the Antiapoptotic Gene Clusterin[1], Neoplasia, , pp. 360–367, vol. 3, No. 4.

Nör et al.; Up–Regulation of Bcl–2 in Microvascular Endothelial Cells Enhances Intratumoral Angiogenesis and Accelerates Tumor Growth; Cancer Research; vol. 61; Mar. 1, 2001; 2183–2188.

Kirby et al.; Bartonella–Associated Endothelial Proliferation Depends on Inhibition of Apoptosis; PNAS; vol. 99, No. 7; Apr. 2, 2002; 4656–4661.

Cox et al.; Angiogenesis and Non–Small Cell Lung Cancer; Lung Cancer; vol. 27, 2000; 81–100.

Tran et al.; A Role for Survivin in Chemoresistance of Endothelial Cells Mediated by VEGF; PNAS; vol. 99, No. 7; Apr. 2, 2002; 4349–4354.

Nör et al.; Engineering and Characterization of Functional Human Microvessels in Immunodeficient Mice; Laboratory Investigation; vol, 81, No. 4; Apr. 2001; 453–463.

Boral et al.; Clinical Evaluation of Biologically Targeted Drugs: Obstacles and Opportunities; Cancer Chemother Pharmacol; vol. 42; 1998, S3–S21.

Zwain et al.; Clusterin Protects Granulosa Cells from Apoptotic Cell Death During Follicular Atresia; Experimental Cell Research; vol. 257; 2000; 101–110.

Lee et al.; In Vitro Models of Prostate Apoptosis: Clusterin as an Antiapopotic Mediator: The Prostate Supplement; vol. 9; 2000; 21–24.

Genta Incorporated; New Data Reaffirm Genta's Molecular Target as Critical Factor for Enhancing Anticancer Treatment; www.genta.com: 2001.

```
                              SEQUENCE LISTING

<160> NUMBER OF SEQ ID NOS: 19

<210> SEQ ID NO 1
<211> LENGTH: 21
<212> TYPE: DNA
<213> ORGANISM: Murine
<220> FEATURE:
<223> OTHER INFORMATION: antisense TRPM-2 ODN

<400> SEQUENCE: 1
gcacagcagg agaatcttca t                                              21

<210> SEQ ID NO 2
<211> LENGTH: 21
<212> TYPE: DNA
<213> ORGANISM: Murine
<220> FEATURE:
<223> OTHER INFORMATION: mismatch control

<400> SEQUENCE: 2
gcacagcagc aggatcttca t                                              21

<210> SEQ ID NO 3
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 3
tggagtcttt gcacgcctcg g                                              21

<210> SEQ ID NO 4
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 4
cagcagcaga gtcttcatca t                                              21

<210> SEQ ID NO 5
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 5
attgtctgag accgtctggt c                                              21

<210> SEQ ID NO 6
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 6
```
ccttcagctt tgtctctgat t                    21

```
<210> SEQ ID NO 7
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 7
```
agcagggagt cgatgcggtc a                    21

```
<210> SEQ ID NO 8
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 8
```
atcaagctgc ggacgatgcg g                    21

```
<210> SEQ ID NO 9
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 9
```
gcaggcagcc cgtggagttg t                    21

```
<210> SEQ ID NO 10
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 10
```
ttcagctgct ccagcaagga g                    21

```
<210> SEQ ID NO 11
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 11
```
aatttagggt tcttcctgga g                    21

```
<210> SEQ ID NO 12
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 12
```
gctgggcgga gttgggggcc t                    21

```
<210> SEQ ID NO 13
<211> LENGTH: 18
<212> TYPE: DNA
<213> ORGANISM: Murine
<220> FEATURE:
```

```
<223> OTHER INFORMATION: antisense Bcl-2 ODN

<400> SEQUENCE: 13
tctcccggct tgcgccat                                                   18

<210> SEQ ID NO 14
<211> LENGTH: 18
<212> TYPE: DNA
<213> ORGANISM: Murine
<220> FEATURE:
<223> OTHER INFORMATION: mismatch Bcl-2 ODN

<400> SEQUENCE: 14
tctcccggca tggtgcat                                                   18

<210> SEQ ID NO 15
<211> LENGTH: 21
<212> TYPE: DNA
<213> ORGANISM: HUMAN

<400> SEQUENCE: 15
cagcagcaga gtatttatca t                                               21

<210> SEQ ID NO 16
<211> LENGTH: 23
<212> TYPE: DNA
<213> ORGANISM: HUMAN

<400> SEQUENCE: 16
aaggaaattc aaaatgctgt caa                                             23

<210> SEQ ID NO 17
<211> LENGTH: 23
<212> TYPE: DNA
<213> ORGANISM: HUMAN

<400> SEQUENCE: 17
acagacaaga tctcccggca ctt                                             23

<210> SEQ ID NO 18
<211> LENGTH: 21
<212> TYPE: DNA
<213> ORGANISM: HUMAN

<400> SEQUENCE: 18
tgcttttaac tctggtaaag t                                               21

<210> SEQ ID NO 19
<211> LENGTH: 21
<212> TYPE: DNA
<213> ORGANISM: HUMAN

<400> SEQUENCE: 19
atatttggca ggtttttctg a                                               21
```

TRPM-2 ANTISENSE THERAPY USING AN OLIGONUCLEOTIDE HAVING 2'-O-(2-METHOXY)ETHYL MODIFICATIONS

CROSS REFERENCE TO RELATED APPLICATIONS

This application is a continuation-in-part of U.S. patent application Ser. No. 09/944,326 filed Aug. 30, 2001 and Ser. No. 09/913,325 filed Aug. 10, 2001, of which Ser. No. 09/913,325 is a Section 371 National Phase Application of PCT/US00/04875 filed Feb. 25, 2000, and claims the benefit of U.S. Provisional Patent Application No. 60/121,726, filed Feb. 26, 1999, all of which are incorporated herein by reference.

BACKGROUND OF THE INVENTION

This application relates to antisense treatments for cancer making use of an antisense oligonucleotide that binds to testosterone-repressed prostate message-2 (TRPM-2).

Prostate cancer is the most common cancer that affects men, and the second leading cause of cancer deaths in men in the Western world. Because prostate cancer is an androgen-sensitive tumor, androgen withdrawal, for example via castration, is utilized in some therapeutic regimens for patients with advanced prostate cancer. Androgen withdrawal leads to extensive apoptosis in the prostate tumor, and hence to a regression of the disease. However, castration-induced apoptosis is not complete, and a progression of surviving tumor cells to androgen-independence ultimately occurs. This progression is the main obstacle to improving survival and quality of life, and efforts have therefore been made to target androgen-independent cells. These efforts have focused on non-hormonal therapies targeted against androgen-independent tumor cells (Yagoda et al., Cancer 71 (Supp. 3): 1098–1109 (1993); Oh et al., J. Urol. 60: 1220–1229 (1998)), however, so far no non-hormonal agent has improved survival.

TRPM-2 is a ubiquitous protein, with a diverse range of proposed activities. In prostate epithelial cell, expression of TRPM-2 increases immediately following castration, reaching peak levels in rat prostate cells at 3 to 4 days post castration, coincident with the onset of massive cell death. These results have led some researchers to the conclusion that TRPM-2 is a marker for cell death, and a promoter of apoptosis. On the other hand, the observation that Sertoli cells and some epithelial cells express high levels of TRPM-2 without increased levels of cell death, raises questions as to whether this conclusion is correct.

Sensibar et al., Cancer Research 55: 2431–2437(1995) reported on in vitro experiments performed to more clearly elucidate the role of TRPM-2 in prostatic cell death. They utilized LNCaP cells transfected with a gene encoding TRPM-2 and observed whether expression of this protein altered the effects of tumor necrosis factor α (TNFα), to which LNCaP cells are very sensitive, with cell death normally occurring within about 12 hours. Treatment of the transfected LNCaP cells with TNFα was shown to result in a transient increase in TRPM-2 levels for a period of a few hours, but these levels had dissipated by the time DNA fragmentation preceeding cell death was observed. Using an antisense molecule corresponding to the bases 1–21 of the TRPM-2 sequence, but not other TRPM-2 antisense oligonucleotides, resulted in a substantial reduction in expression of TRPM-2, and an increase in apoptotic cell death in LNCaP cells exposed to TNFα. This led Sensibar et al. to the hypothesis that overexpression of TRPM-2 could protect cells from the cytotoxic effect of TNF α, and that TRPM-2 depletion is responsible for the onset of cell death, although the mechanism of action remains unclear.

While Sensibar, et al. provides information about the possible role of TRPM-2, it nevertheless discloses results from only a model system in which expression of TRPM-2 is based on a transfected gene. Furthermore, expression levels of TRPM-2 is very low or absent in LNCaP cells grown in other labs. The situation which results in vivo when prostate tumor cells are subjected to androgen withdrawal is far more complex, with numerous proteins changing expression levels as a result. Thus, it is not possible from the Sensibar, et al. data to predict whether TRPM-2 would perform the same function when present in combination with other proteins, or whether changes in levels of TRPM-2 following androgen withdrawal in vivo could provide any therapeutic benefits. Indeed, the fact that TRPM-2 is expressed in substantial quantities in prostatic tumor cells at various stages following androgen withdrawal, including stages where significant apoptotic cell death is occurring suggests that role of TRPM-2 in vivo may be more complicated.

While the art provides data concerning certain aspects of apoptotic cell death in prostatic tumor cells, it offers neither a teaching nor a suggestion of a methodology to provide a delay in the onset of androgen-independence.

SUMMARY OF THE INVENTION

The present invention provides a compound consisting of an oligonucleotide of sequence CAGCAGCAGAGTCT-TCATCAT; SEQ ID NO: 4, where the oligonucleotide has a phosphorothioate backbone throughout, the sugar moieties of nucleotides 1–4 and 18–21 bear 2'-O-methoxyethyl modifications, and the remaining nucleotides (nucleotides 5–17) are 2'-deoxynucleotides, and where the cytosines of nucleotides 1, 4 and 19 are 5-methylcytosines. This new compound was found to have increased stability in vivo and to have improved in vitro and in vivo antitumor activity. This compound can be used for delaying progression of prostatic tumor cells to an androgen-independent state, for treating prostate cancer in an individual suffering from prostate cancer, for enhancing the chemo- or radiation sensitivity of cancer cells in an individual suffering from a cancer that expresses TRPM-2 in amounts different from normal tissue of the same type, and for delaying of progression of a population of prostatic tumor cells from a state in which living prostatic tumor cells are androgen-sensitive to a state in which living tumor cells are androgen independent.

DETAILED DESCRIPTION OF THE INVENTION

The present invention relates to the antisense TRPM-2 oligonucleotide ISIS 112989, which is a 21mer oligonucleotide (CAGCAGCAGAGTCTTCATCAT; SEQ ID NO: 4) targeted to the translation initiation codon and next 6 codons of the human TRPM-2 sequence (Genbank accession no: NM_001831). ISIS 112989 is also referred to herein as 2'-MOE modified TRPM-2 antisense oligonucleotide and 2'-MOE ASO. The oligonucleotide has a phosphorothioate backbone throughout. The sugar moieties of nucleotides 1–4 and 18–21 (the "wings") bear 2'-O-methoxyethyl modifications and the remaining nucleotides (nucleotides 5–17; the "deoxy gap") are 2'-deoxynucleotides. Cytosines in the wings (i.e., nucleotides 1, 4 and 19) are 5-methylcytosines. The present invention also relates to the use of ISIS 112989 compositions in the treatment of cancer. The invention can be applied in the treatment of cancers where the cancer cells express TRPM-2. Significant classes of cancer cells which express TRPM-2 include prostate cancer cells, human renal cell cancer (RCC) cells, non-small cell lung cancer cells, urothelial transitional cancer cells, ovarian cancer cells, and some breast cancer cells.

As reported in the parent applications (U.S. patent application Ser. No. 09/944,326 filed Aug. 30, 2001 and Ser. No. 09/913,325 filed Aug. 10, 2001), enhancement of castration-induced tumor cell death and delay of the progression of androgen-sensitive prostatic cancer cells to androgen-independence is achieved by inhibiting the expression of TRPM-2 by the cells. Experiments were performed in three model systems, the in vivo Shionogi tumor model, the human TRPM-2 transfected LNCaP model, and the human PC-3 model, which taken together demonstrated that such inhibition leading to delay of androgen-independence can be achieved by treating androgen-sensitive prostatic tumor cells with antisense oligodeoxynucleotides (ODNs).

Figure 1:
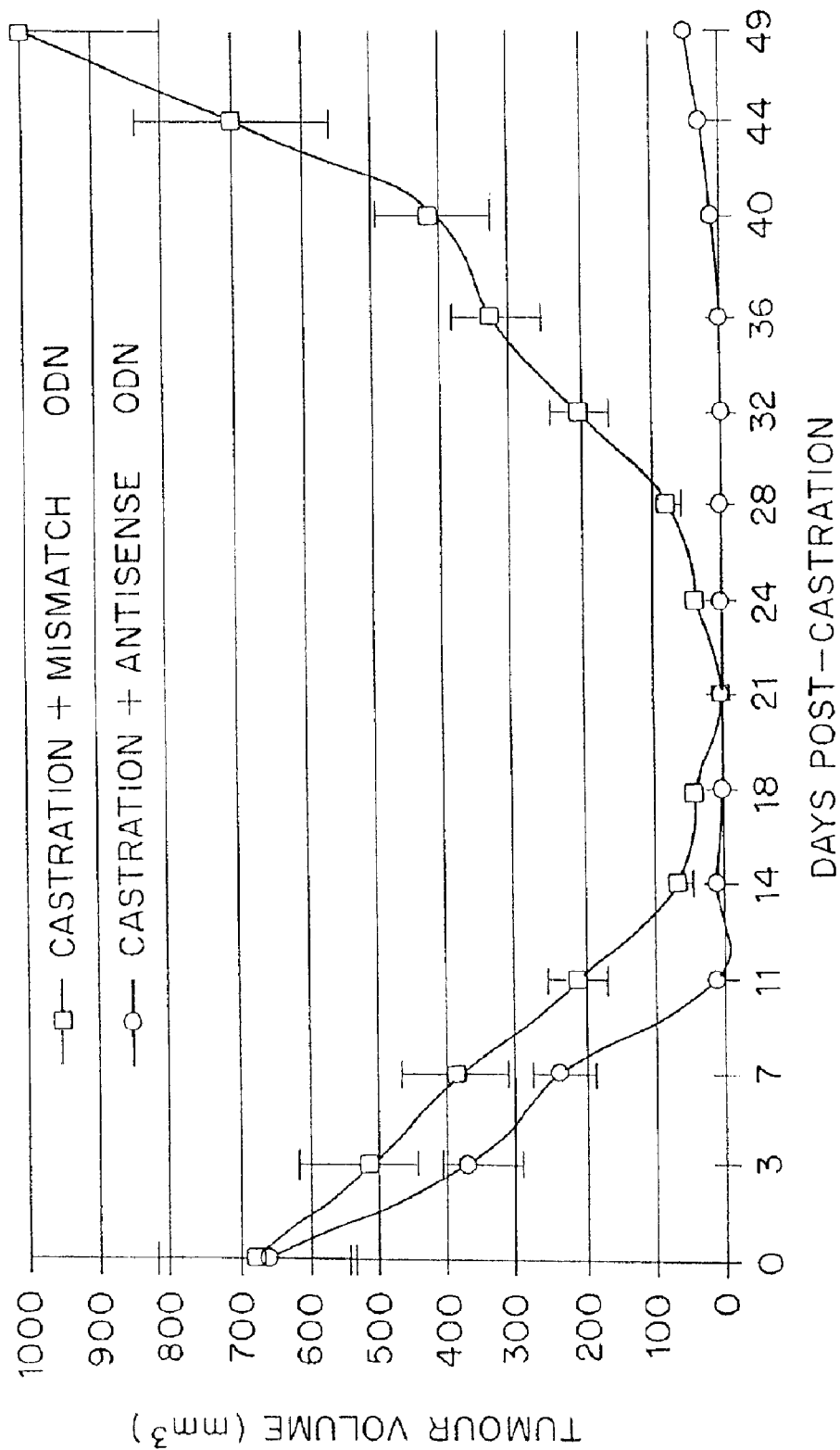
FIG. 1 shows the delay in onset of androgen-independence which is achieved using an antisense TRPM-2 ODN.

In the first experiment reported in the parent applications, the ability of a mouse TRPM-2 antisense molecule, (Seq. ID. No. 1) to delay onset of androgen independence in the Shionogi tumor model was evaluated. The ability of the antisense ODNs that inhibit expression of TRPM-2 to delay the onset of androgen-independence was evaluated by measuring tumor volume post-castration in the Shionogi tumor model. The test animals (n=7) were treated intraperitoneally once daily with 12.5 mg/kg repeat doses of antisense TRPM-2 ODNs (Seq. ID. No 1) in a buffered saline solution. As a control, animals (n=7) were treated with a mismatch ODN (Seq. ID. No. 2). As shown in FIG. 1, both test and control groups showed the expected decline in tumor volume immediately following castration, but the tumors in the antisense TRPM-2 ODN-treated mice regressed faster than the controls. The control group also exhibited the expected increase in tumor volume which is associated the development of androgen-independence. In contrast, at 49 days post-castration, little tumor regrowth had occurred in the mice treated using the antisense TRPM-2 ODN. Tumors did eventually recur in the antisense TRPM-2 ODN-treated mice, but the median time to recurrence is approximately twice that of the control group. Thus, inhibition of TRPM-2 is effective not only for increasing the amount of cell death which occurs immediately following androgen withdrawal, but also for delaying the onset of androgen-independence. The more rapid decrease in tumor volume in the mice treated with antisense TRPM-2 ODNs was due to earlier onset and more extensive castration-induced apoptosis. This was confirmed by detecting poly(ADP-ribose) polymerase (PARP) cleavage fragments in Shionogi tumor specimens (Miyake, et al., *Cancer Res.* 60:170–176 (2000)).

Figure 2:
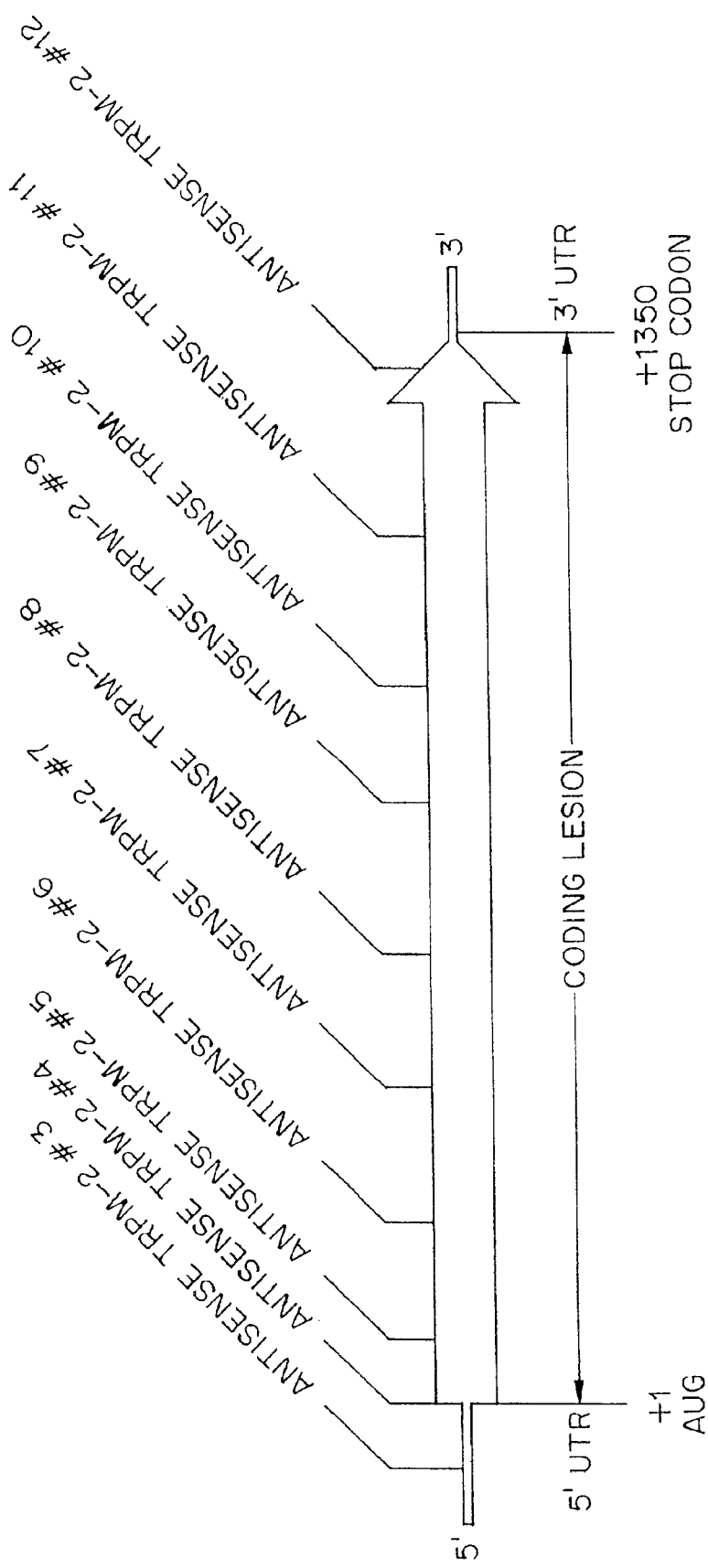
FIG. 2 shows the positions of 10 antisense oligonucleotides evaluated for the ability to inhibit TRPM-2 expression and delay onset of androgen-independence.
Figure 3:
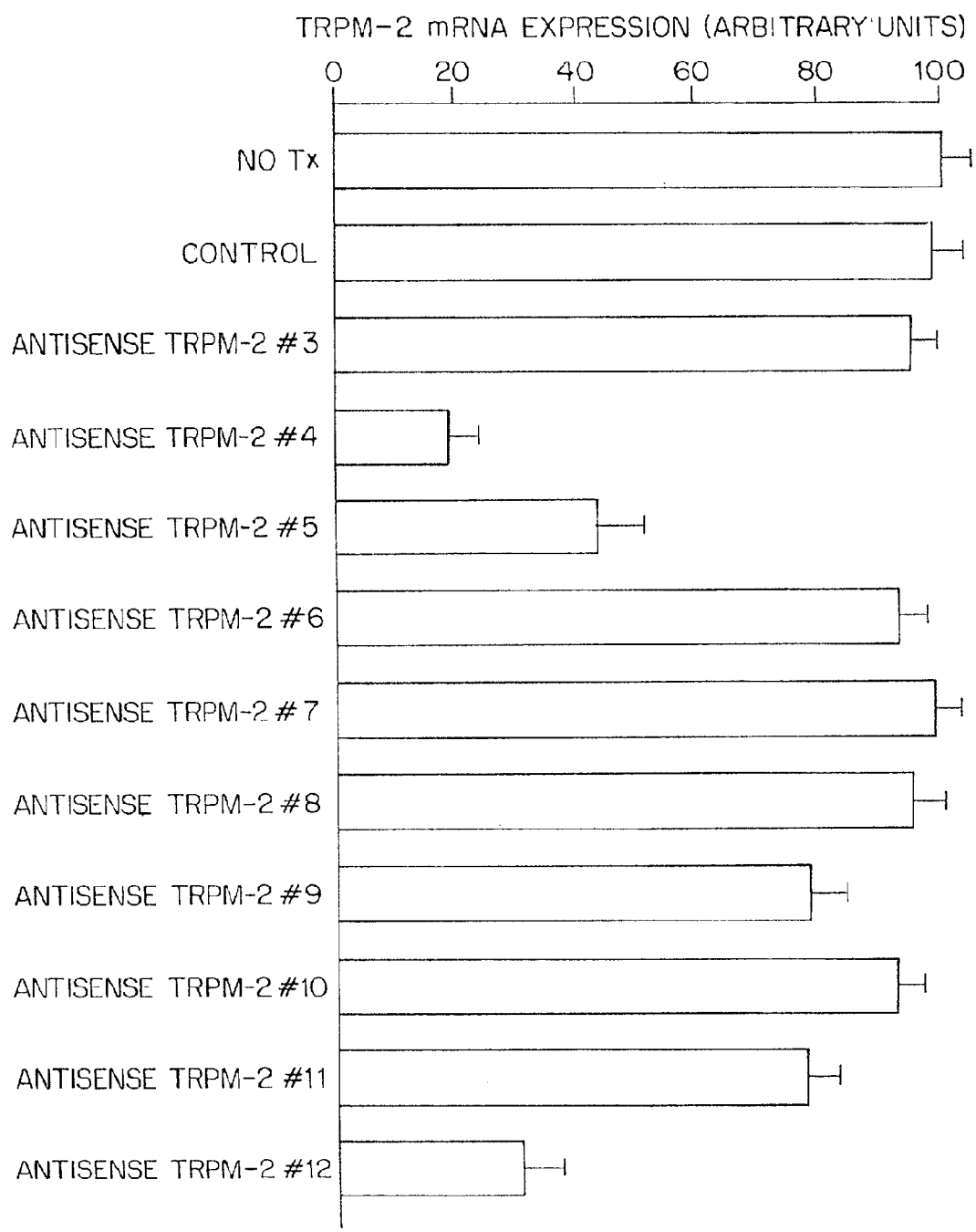
FIG. 3 shows expression levels of TRPM-2 mRNA in the presence of various antisense ODNs.

In the parent applications, experiments were reported on the evaluation of which human antisense ODNs complementary to TRPM-2 mRNA sequences are most effective for this purpose. A series of ten antisense phosphorothioate ODNs were prepared spanning various mRNA regions as shown in FIG. 2. The sequences of these ten ODNs are set forth in the attached Sequence Listing as Seq. ID. Nos. 3–12. The ten human antisense ODNs were evaluated using TRPM-2 transfected LNCaP cells and human prostate cancer PC-3 cells for their ability to inhibit expression of TRPM-2 mRNA. As shown in FIG. 3, the antisense ODNs tested produced variable levels of inhibition of TRPM-2 mRNA expression, with the best results being achieved with Seq. ID Nos. 4, 5, and 12. Sequence ID No. 5 corresponds to the sequence used by Sensibar, et al. that produced inhibition of TRPM-2 expression in LNCaP cells, and is complementary to the first 21 bases of the TRPM-2 mRNA. The most effective down-regulation occurred with Seq. ID No. 4. Common to all of the effective sequences is an overlap with either the initiation or termination sites of the TRPM-2 mRNA. Thus, it was shown that inhibition of expression of TRPM-2 may be accomplished by the administration of antisense ODNs, particularly antisense ODNs which are complementary to a region of the TRPM-2 mRNA spanning either the translation initiation site or the termination site.

It was also reported in the parent applications that therapeutic treatment of individuals, including human individuals, suffering from prostate cancer can be achieved by initiating androgen-withdrawal to induce apoptotic cell death of prostatic tumor cells in the individual, and administering to the individual a composition effective to inhibit expression of TRPM-2 by the tumor cells, thereby delaying the progression of prostatic tumor cells to an androgen-independent state in an individual. Initiation of androgen withdrawal may be accomplished via surgical (removal of both testicles) or medical (drug-induced suppression of testosterone) castration, which is currently indicated for treatment of prostate cancer. Medical castration can be achieved by various regimens, including LHRH agents or antiandrogens. (Gleave et al., *CMAJ* 160: 225–232 (1999)). Intermittent therapy in which reversible androgen withdrawal is effected is described in Gleave et al. *Eur. Urol.* 34 (Supp. 3): 37–41 (1998). The inhibition of TRPM-2 expression may be transient, and ideally should occur coincident with androgen withdrawal. In humans, this means that inhibition of expression should be effective starting within a day or two of androgen withdrawal and extending for about 3 to 6 months.

It was also reported in the parent applications that antisense TRPM-2 ODNs have been determined to enhance chemosensitivity in human renal cell cancer (RCC). RCC is a chemoresistant disease with no active chemotherapeutic agent with objective response rates higher than 10%. Increased TRPM-2 expression in renal proximal convoluted cells undergoing apoptosis has been observed after various stimuli including ureteral obstruction and aminoglycosides. The functional significance of TRPM-2 expression in RCC has not been well documented, however, test results showed that antisense TRPM-2 ODN enhances chemosensitivity in human RCC CaKi-2 cells (See Example 6, infra). Antisense TRPM-2 ODNs were also found to increase sensitivity to radiation (See Example 7 and FIG. 8).

In the parent applications, it was reported that the ODNs employed could be modified to increase their stability in vivo. For example, the ODNs may be employed as phosphorothioate derivatives (replacement of a non-bridging phosphoryl oxygen atom with a sulfur atom) which have increased resistance to nuclease digestion. 2'-MOE (2'-O-(2-methoxyethyl) modification (ISIS backbone) is also effective and improves the in vitro and in vivo antitumor activity of antisense TRPM-2 oligonucleotides.

The present invention discloses a 2'-MOE modified antisense oligonucleotide (ISIS 112989, as described above), methods for using ISIS 112989 for enhancing castration-induced tumor cell death and delaying the progression of prostatic tumor cells to androgen independence and for the treatment of individuals, including humans, suffering from prostate cancer, and therapeutic agents containing ISIS 112989 that are effective for use in such methods. The therapeutic method of the invention will most commonly be used in the treatment of individuals with advanced prostate cancer.

Administration of ISIS 112989 can be carried out using the various mechanisms known in the art, including naked administration and administration in pharmaceutically acceptable lipid carriers. For example, lipid carriers for antisense delivery are disclosed in U.S. Pat. Nos. 5,855,911 and 5,417,978 which are incorporated herein by reference. In general, ISIS 112989 is administered by intravenous (i.v.), intraperitoneal (i.p.), subcutaneous (s.c.) or oral routes, or direct local tumor injection. From the experiments using the Shionogi mouse model reported in the parent applications, it appears that the antisense oligonucleotide is preferentially active in the tumor cells.

The amount of ISIS 112989 administered is one effective to inhibit the expression of TRPM-2 in prostatic cells. It will be appreciated that this amount will vary with the nature of any carrier used. The determination of appropriate amounts for any given composition is within the skill in the art, through standard series of tests designed to assess appropriate therapeutic levels.

Figure 12:
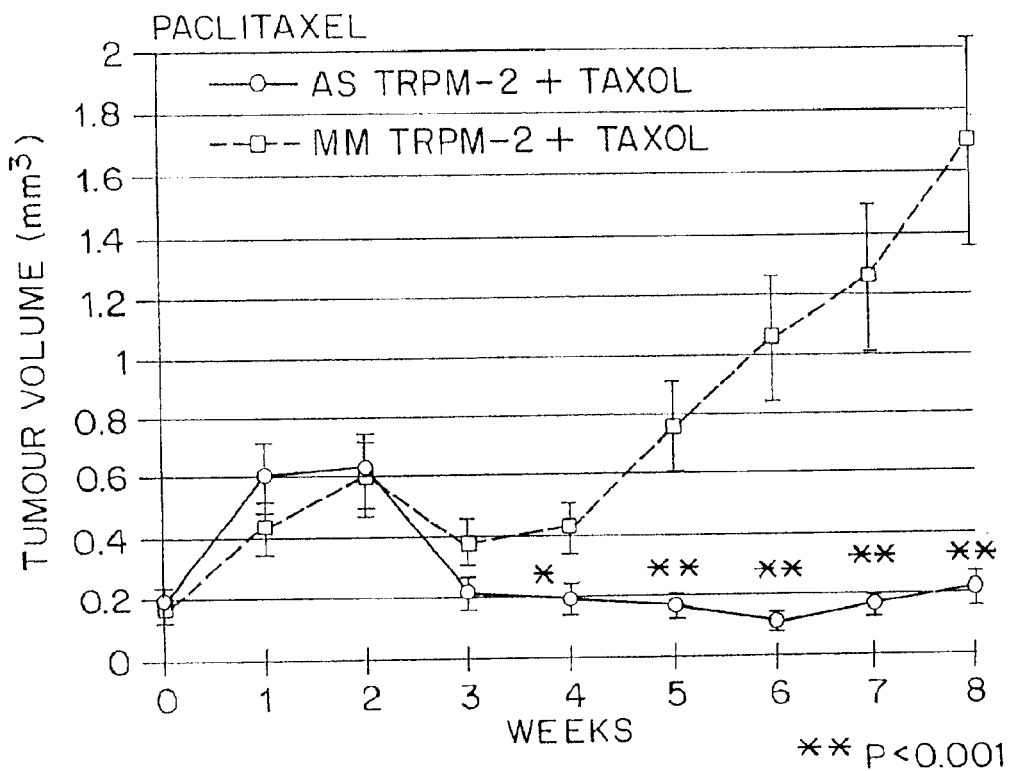
FIGS. 12A and 12B show the increased sensitivity of Shionogi tumor cells to chemotherapy agents paclitaxel and mitoxanthrone when administered with antisense TRPM-2 ODN.
Figure 12:
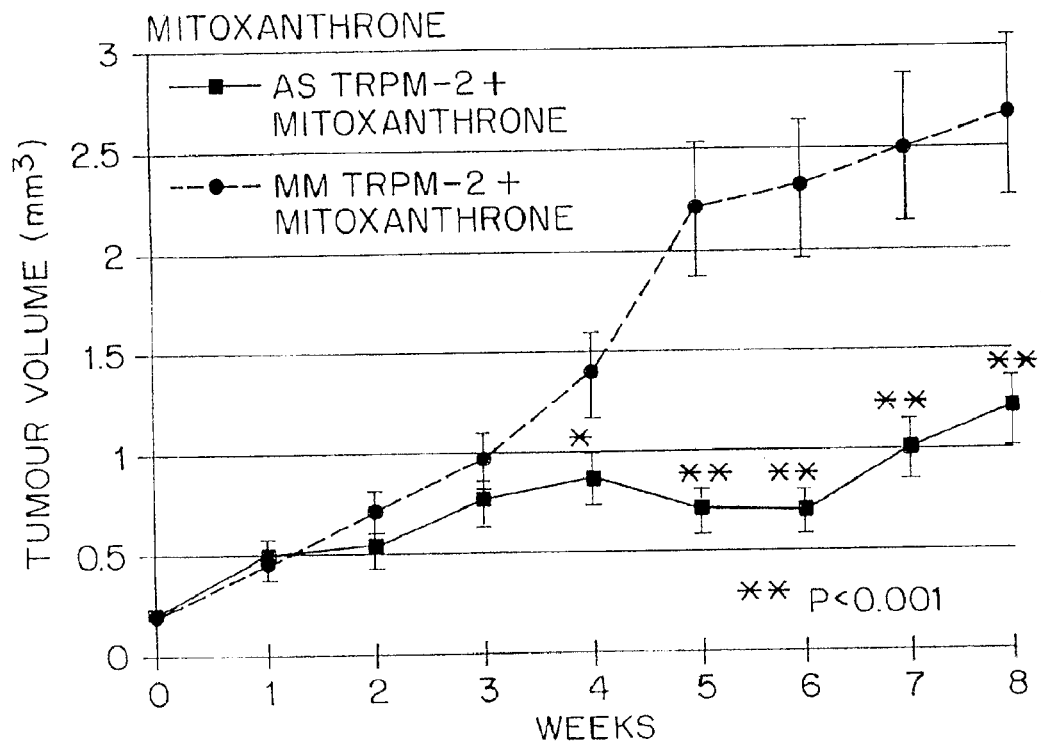

The method for treating prostate cancer in accordance with the invention may further include administration of chemotherapy agents and/or additional antisense oligonucleotides directed at different targets. For example, in the parent applications it was shown using the Shionogi tumor model that antisense TRPM-2 ODN increases sensitivity to conventional chemotherapy agents such as taxanes (paclitaxel or docetaxel) and mitoxanthrone (FIGS. 12A and 12B). As shown in FIGS. 12A and 12B, treatment with antisense TRPM-2 ODN in the presence of taxol or mitoxanthrone resulted in a reduced tumor volume as compared to the combination of taxol or mitoxanthrone with the mismatch (MM) ODN. Other agents likely to show synergistic activity include other cytotoxic agents (e.g. cyclophosphamide, topoisomerase inhibitors), angiogenesis inhibitors, differentiation agents and signal transduction inhibitors. Similarly, it was shown that combinations of TRPM-2 antisense oligonucleotide with other antisense species such as antisense Bcl-2 ODN worked better at killing Shionogi cells in vitro than either ODN alone. Thus, it was shown in the parent applications that TRPM-2 can work in concert with other antisense molecules, such as antisense Bcl-2, Bcl-xl and c-myc oligonucleotide to provide greater effectiveness.

For the present invention, studies were performed comparing the efficacy, tissue half-lives, and toxicity of phosphorothioate antisense oligonucleotide to 2nd generation backbone 2'-O-(2-methoxy)ethyl (2'-MOE) ribose-modified antisense oligonucleotide (ISIS 112989 or 2'-MOE antisense oligonucleotide). The methods and results of these studies are described in Example 13. The results of the studies were that 2'-MOE antisense oligonucleotide and phosphorothioate antisense oligonucleotide decreased TRPM-2 mRNA levels in a dose-dependent and sequence-specific manner. 2'-MOE antisense oligonucleotide more potently suppressed TRPM-2 mRNA compared to phosphorothioate antisense oligonucleotide. $IC_{50}$ of paclitaxel was equally reduced by both compounds. In vivo tissue half-life was significantly longer for 2'-MOE antisense oligonucleotide than for phosphorothioate antisense oligonucleotide. Weekly administration of 2'-MOE antisense oligonucleotide was equivalent to daily phosphorothioate antisense oligonucleotide in enhancing paclitaxel efficacy in vivo. 2'-MOE antisense oligonucleotide potently suppressed TRPM-2-expression and prolonged tissue half-lives with no additional side-effects. These results support the use of 2'-MOE antisense oligonucleotide over conventional phosphorothioate antisense oligonucleotide by potentially increasing potency and allowing longer dosing intervals in clinical trials.

The present invention provides a method for delaying progression of prostatic tumor cells to an androgen-independent state by treating androgen-sensitive prostatic tumor cells in vivo with ISIS 112989, which inhibits expression of TRPM-2 by the tumor cells.

The present invention also provides a method for treating prostate cancer in an individual suffering from prostate cancer. This method involves the steps of initiating androgen-withdrawal to induce apoptotic cell death of prostatic tumor cells in the individual, and administering to the individual a composition effective to inhibit expression of TRPM-2 by the tumor cells, thereby delaying the progression of prostatic tumor cells to an androgen-independent state in an individual. The composition effective to inhibit expression of TRPM-2 is ISIS 112989. This method may contain the further step of administering to the individual a chemotherapy agent. Preferably, the chemotherapy agent is a taxane or mitoxanthrone. The method may contain the further step of administering to the individual a second antisense oligonucleotide which inhibits expression of an anti-apoptotic protein other than TRPM-2. Preferably, the second antisense oligonucleotide is antisense Bcl-2 oligonucleotide. Alternatively, the method may contain a combination of both of these further steps.

The present invention also provides a method for enhancing the chemo- or radiation sensitivity of cancer cells in an individual suffering from a cancer that expresses TRPM-2 in amounts different from normal tissue of the same type. This method involves administering to the individual a composition effective to inhibit expression of TRPM-2 by cancer cells, where the composition effective to inhibit expression of TRPM-2 is ISIS 112989.

The present invention also provides a method for delaying of progression of a population of prostatic tumor cells from a state in which living prostatic tumor cells are androgen-sensitive to a state in which living tumor cells are androgen independent. This method involves treating the population of androgen-sensitive prostatic tumor cells with ISIS 112989, which inhibits expression of TRPM-2 by the tumor cells.

The invention will now be further described with reference to the following, non-limiting examples.

EXAMPLE 1

Shionogi tumor model experiments were performed using cells from the Toronto subline of transplantable SC-115 AD mouse mammary carcinoma. For in vivo studies, approximately $5 \times 10^6$ cells of the Shionogi carcinoma were injected subcutaneously in adult male DD/S strain mice. When the Shionogi tumors became 1 to 2 cm in diameter, usually 2 to 3 week after injection, castration was performed through an abdominal incision under methoxyflurane anesthesia. Details of the maintenance of mice, tumor stock and operative procedures have been previously described. (Bruchovsky et al., *Cancer res.* 50: 2275–2282 (1990); Rennie et al., *Cancer Res.* 48: 6309–6312 (1988); Bruchovsky et al., *Cell* 13: 272–280 (1978); Gleave et al., in *Genitourinary Oncology*, pp. 367–378, Lange et al., eds, Lippencott (1997); Gleave et al., *J. Urol.* 157: 1727–1730 (1997); Bruchovsky et al., *The Prostate* 6: 13–21 (1996)).

Mice were randomly selected for treatment with murine phosphorothioate antisense TRPM-2 ODN (Seq. ID No. 1) or a mismatch control (Seq. ID No. 2) which is two bases different in sequence from the antisense TRPM-2 ODN. Each experimental group consisted of 7 mice. One day after castration, 12.5 mg/kg of antisense TRPM-2 or mismatch control ODN dissolved in phosphate buffered saline were injected intraperitoneally once daily into each mouse of 40 days. Tumor volume was measured twice weekly, and calculated by the formula length×width×depth×0.5236. Gleave et al., *Cancer Res.* 52: 1598–1605 (1992). Data points were reported as average tumor volumes±standard deviation.

The results of this study are shown in FIG. 1. As shown, Shionogi tumors regressed faster and complete regression occurred earlier in mice treated with antisense TRPM-2 ODN. Furthermore, treatment with antisense TRPM-2 ODN substantially delayed the onset of androgen-independence which is reflected by the increase in tumor volume after day 21 in the control animals. No side effects associated with antisense TRPM-2 or the mismatch control were observed.

To examine the effects of in vivo ODN treatment on levels of TRPM-2 mRNA, Northern blot analysis was performed on Shionogi tumor tissue from mice. The mice were treated daily with 12.5 mg/kg of antisense TRPM-2 ODN (n=6) or the mismatch control (n=6) by intraperitoneal injection starting one day after castration. On the fourth day after castration, tumor tissues were harvested and analyzed by Northern blot for TRPM-2 mRNA. Antisense TRPM-2 ODN resulted in a 75% reduction in TRPM-2 mRNA levels in Shionogi tumors compared to mismatch control ODN treated tumors. (FIG. 3).

Comparable analyses were performed on normal mouse organs. Samples of spleen, kidney, prostate and brain were harvested from Shionogi tumor mice treated with antisense TRPM-2 ODN and mismatch control under the same treatment schedule, and analyzed by Northern blot. Although TRPM-2 mRNA levels was significantly lower in tumor tissues, antisense TRPM-2 ODN had no effect on TRPM-2 mRNA levels in the normal organs.

EXAMPLE 2

The sequence selectivity of the antisense TRPM-2 ODN (Seq. ID. No. 1) was confirmed by comparing expression levels of TRPM-2 mRNA in Shionogi tumor cells maintained in vitro, after treatment with the varying levels of antisense TRPM-2 ODN or a mismatch control (Seq. ID. No. 2). To facilitate uptake of the ODNs into the cells, the ODNs were formulated in a cationic lipid carrier (Lipofectin, (Life Technologies, Inc.)). Cells were treated twice over a period of two days using the following protocol. Cells were preincubated for 20 minutes with 4 µg/ml of lipofectin in serum free OPTI-MEM (Life Technologies, Inc.) and then incubated with the medium containing the selected concentration of ODN and lipofectin for four hours. The medium was then replaced with the standard culture medium.

Figure 4:
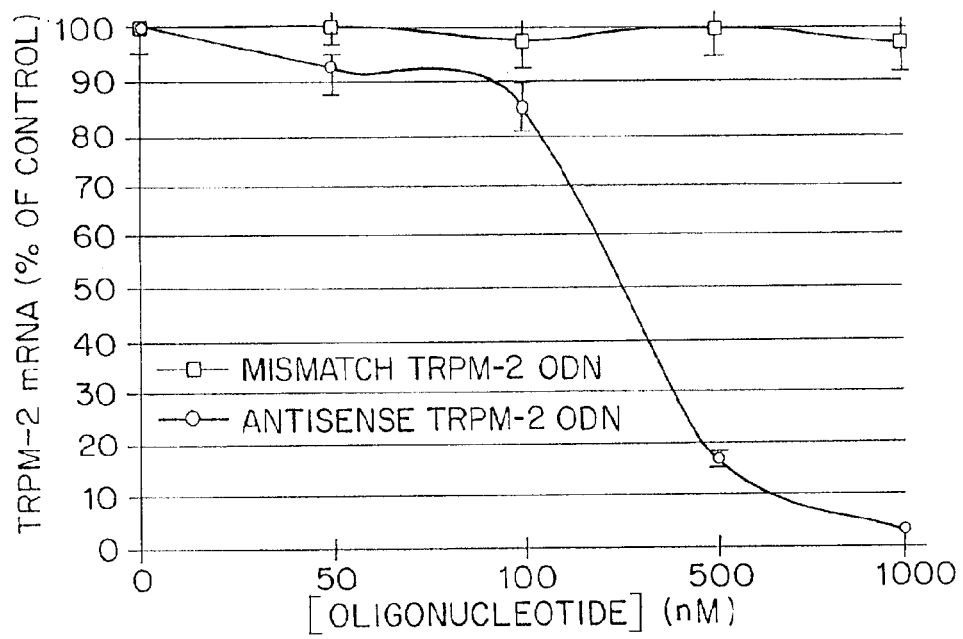
FIG. 4 shows the levels of TRPM-2 mRNA in Shionogi cells treated in vitro with varying amounts of antisense TRPM-2 ODN or a mismatch control.

The amount of TRPM-2 mRNA in the cells was evaluated using Northern blot analysis. As shown in FIG. 4, treatment of Shionogi cells with antisense TRPM-2 ODN reduced TRPM-2 mRNA levels in a dose dependent manner. In contrast, TRPM-2 mRNA levels were not affected by the mismatch ODN (Seq. ID. No. 2) at any of the employed concentrations. Thus, the affect of antisense TRPM-2 ODN is apparently sequence specific.

EXAMPLE 3

Figure 5:
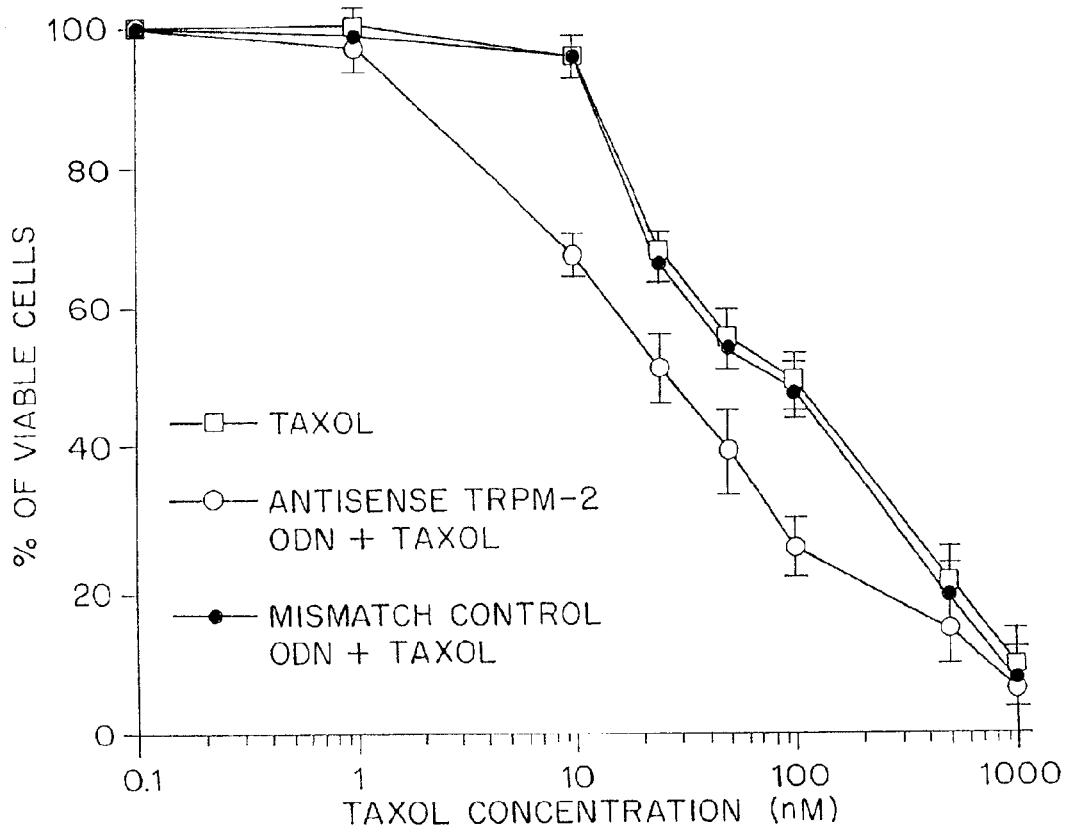
FIG. 5 shows the dose-response curve for combinations of taxol and antisense TRPM-2 ODN.

Shionogi cells maintained in vitro were treated with varying amounts of taxol alone or in combination with 500 nM antisense TRPM-2 ODN (Seq. ID. No. 1) or the mismatch control (Seq. ID No. 2). The cells were treated twice, as described in Example 2, and the percentage of viable cells remaining was determined. The results are summarized in FIG. 5. As shown, the inclusion of antisense TRPM-2 ODN shifted the dose-response curve to the left, lowering the $IC_{50}$ by a factor of 5 to 10. Similar results were achieved using mitoxanthrone in place of paclitaxel (FIGS. 12A and 12B).

EXAMPLE 4

Figure 6:
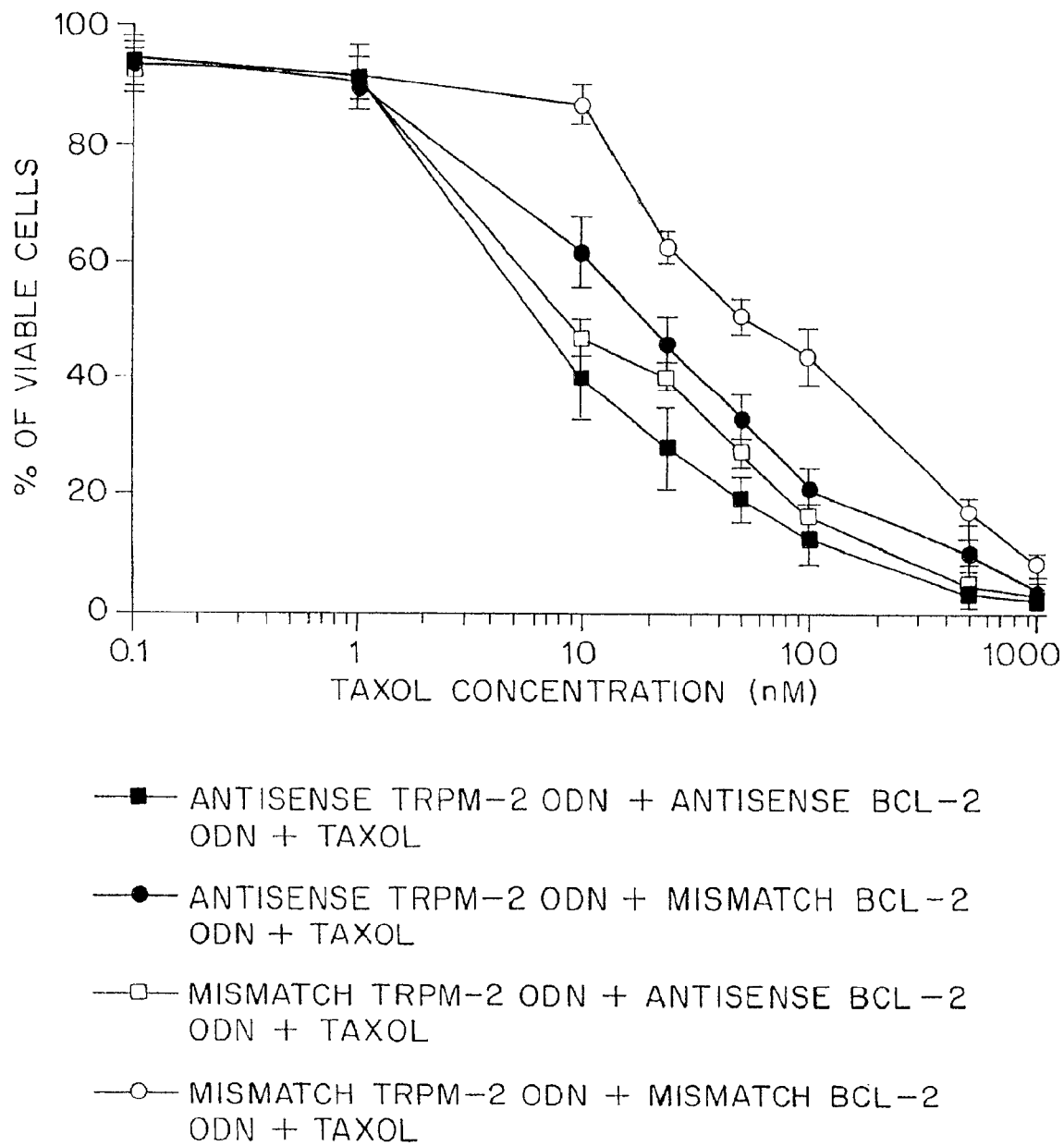
FIG. 6 shows the dose-response curve for combinations of taxol, antisense TRPM-2 ODN and antisense Bcl-2 ODN.

The experiment of Example 3 was repeated, with the addition of antisense Bcl-2 ODN (Seq. ID. No. 13) or a mismatch Bcl-2 ODN (Seq. ID. No. 14) in various combinations with antisense/mismatch TRPM-2 ODN and taxol. The results are shown in FIG. 6. The combination of antisense TRPM-2 ODN with antisense Bcl-2 ODN and taxol further enhanced the cytotoxic effects of taxol. Thus, the targeting of additional anti-apoptotic agents appears to provide therapeutic benefits.

EXAMPLE 5

To identify appropriate antisense TRPM-2 ODN sequences for use in human therapy, antisense ODN sequences directed against 10 different sites of the human TRPM-2 gene (FIG. 2, Seq. ID Nos. 3–12) were synthesized and tested for their ability to decrease TRPM-2 gene expression in human prostate cancer PC-3 and transfected LNCaP cells that overexpress TRPM-2 using the same treatment protocol described in Example 2. The results are summarized in FIG. 3. As shown, sequences 4, 5 and 12 are active for reduction of TRPM-2 expression. These three sequences overlap or are immediately adjacent to the translation initiation or termination sites.

EXAMPLE 6

Immunohistochemical staining was used to characterize TRPM-2 expression in 17 RCC and normal kidney tissues obtained from radical nephrectomy specimens. TRPM-2 expression in human renal cancer cell lines ACHN, CaKi-1 and CaKi-2 was evaluated by Northern and Western blot analyses. Northern blot analysis was used to assess changes in TRPM-2 mRNA expression after antisense TRPM-2 ODN treatment. The effects of combined antisense TRPM-2 ODN and taxol treatment on CaKi-2 cell growth was examined using a MTT assay (Zellweger et al., *Neoplasia* 3: 360–367 (2001)).

Immunostaining showed an increased TRPM-2 expression in 11 RCC specimens in comparison to the adjacent normal kidney tissue. In the remaining 6 cases, no difference was seen between malignant and normal tissue. Both TRPM-2 mRNA and protein expression were detectable in all three human RCC cell lines, with highest levels for CaKi-2.

Figure 7A:
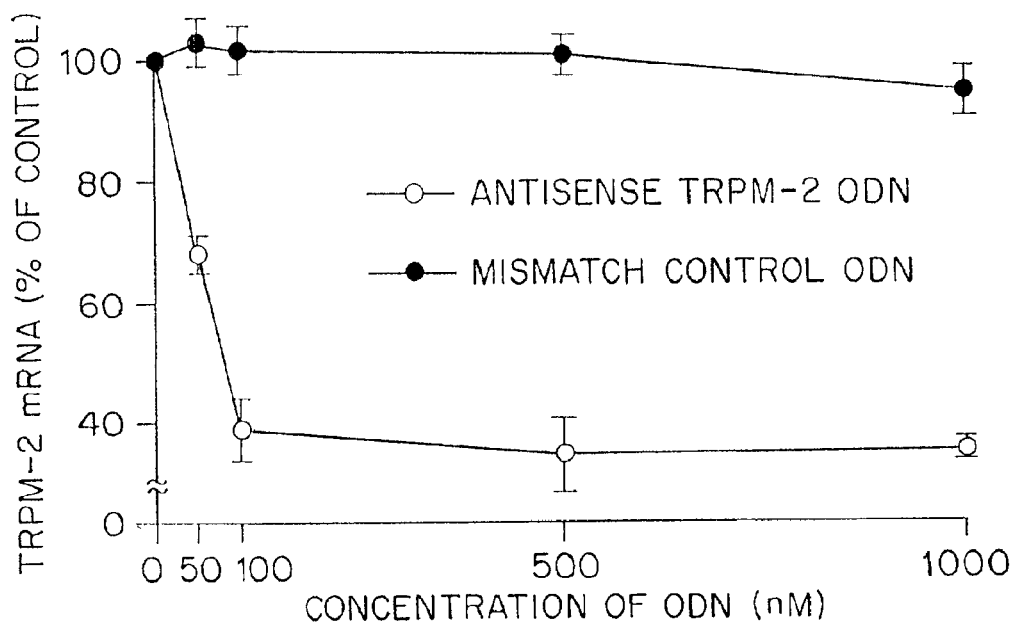
FIG. 7A shows decease in TRPM-2 mRNA levels in human renal cell cancer after treatment with antisense TRPM-2 ODNs.
Figure 7B:
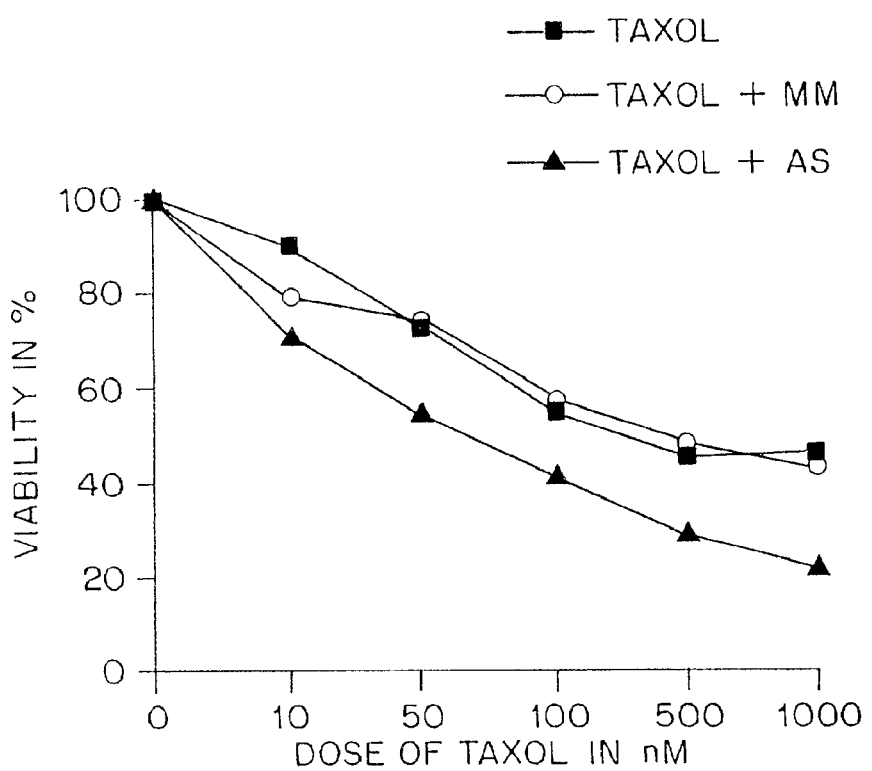
FIG. 7B shows the increase in chemosensitivity of human renal cell cancer to taxol after treatment with antisense TRPM-2 ODNs.

Antisense TRPM-2 ODN (Seq. ID. No. 1), but not mismatch control ODN (Seq. ID. No. 2), inhibited TRPM-2 expression in CaKi-2 cells in a dose dependant and sequence specific manner (FIG. 7A). Furthermore, antisense TRPM-2 ODN substantially enhanced taxol chemosensitivity, reducing IC50 of taxol by 1 log (500 nM to 50 nM) compared to mismatch control ODN (FIG. 7B). These data demonstrate that TRPM-2 and its protein, clusterin, are expressed at higher levels in RCC compared to normal kidney tissue, and that antisense TRPM-2 ODN may be useful in enhancing the cytotoxic effects of conventional chemotherapy in advanced RCC.

EXAMPLE 7

Figure 8:
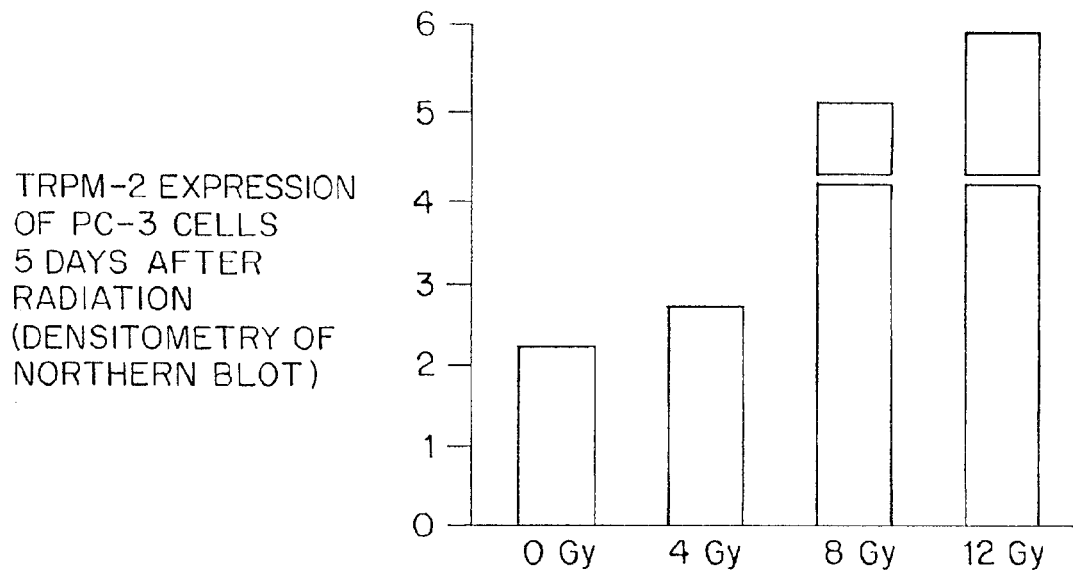
FIG. 8 shows TRPM-2 expression in PC-3 prostate cancer cells after various doses of radiation.
Figure 10:
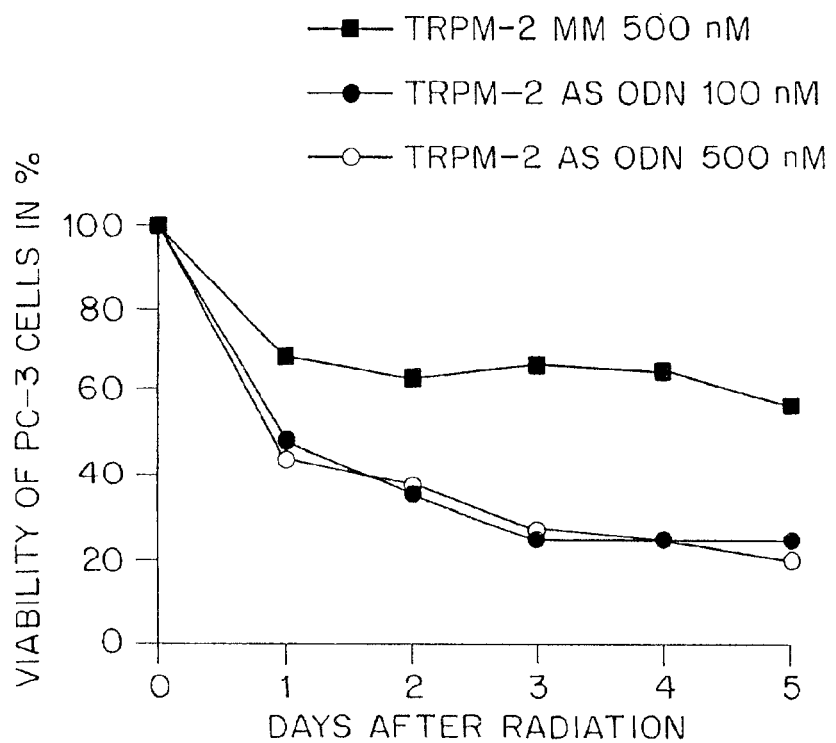
FIG. 10 shows the increased susceptibility of PC-3 cells to radiation after treatment with antisense TRPM-2 ODN.
Figure 9A:
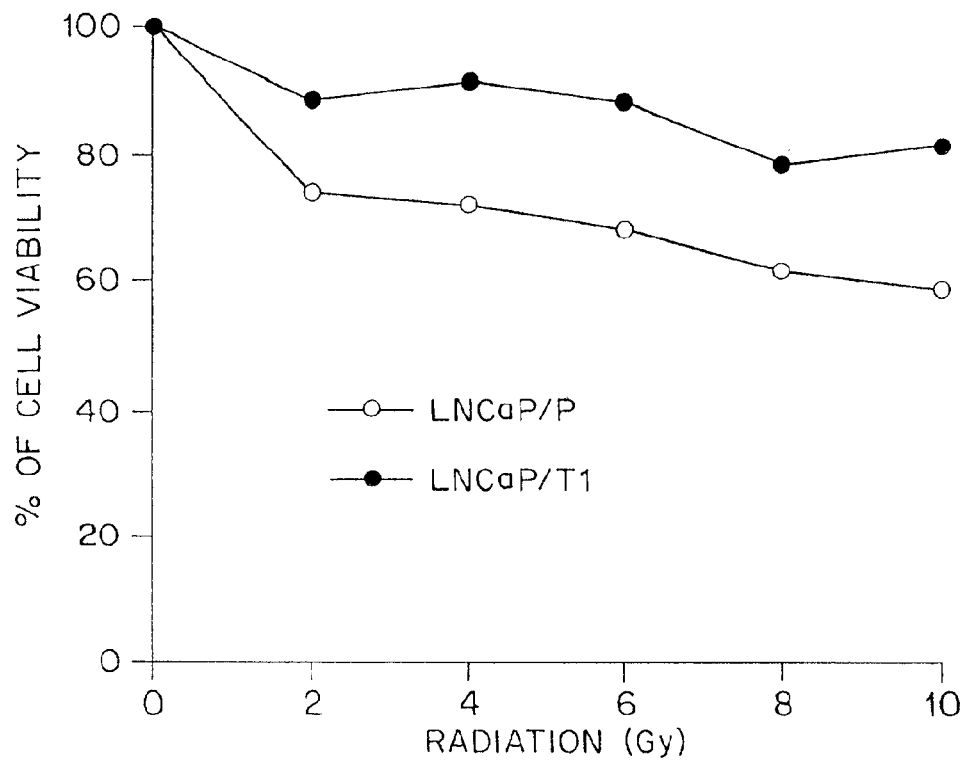
FIGS. 9A and 9B show the comparative radiation resistance of human prostate cell lines which overexpress (LNCaP/T) and normally (LNCaP/P) express TRPM-2.
Figure 9B:
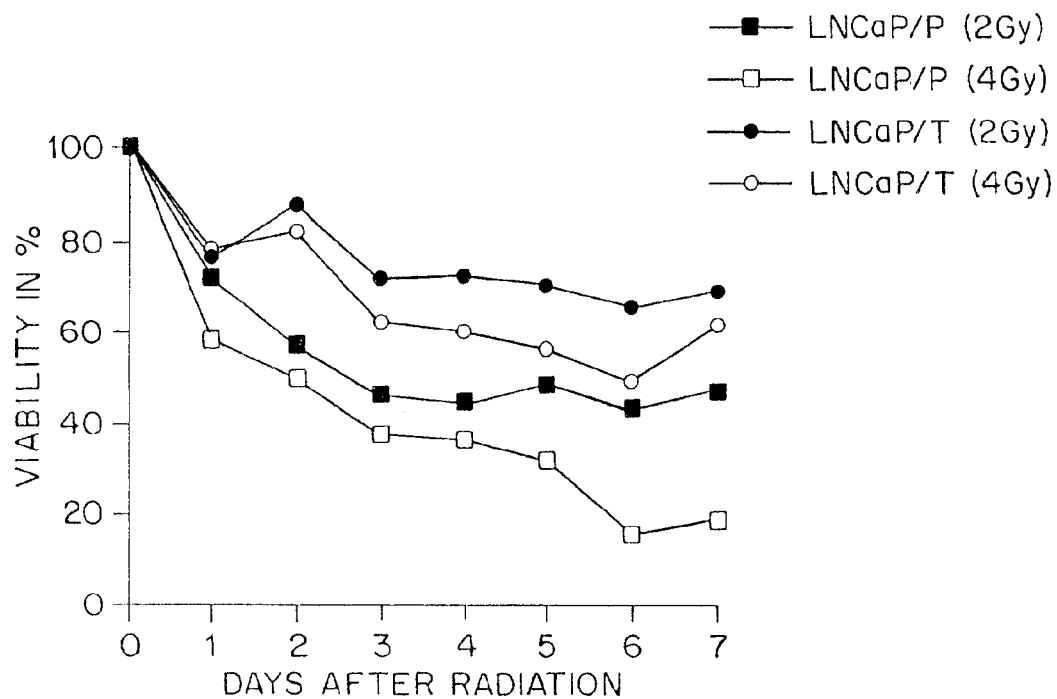
Figure 11A:
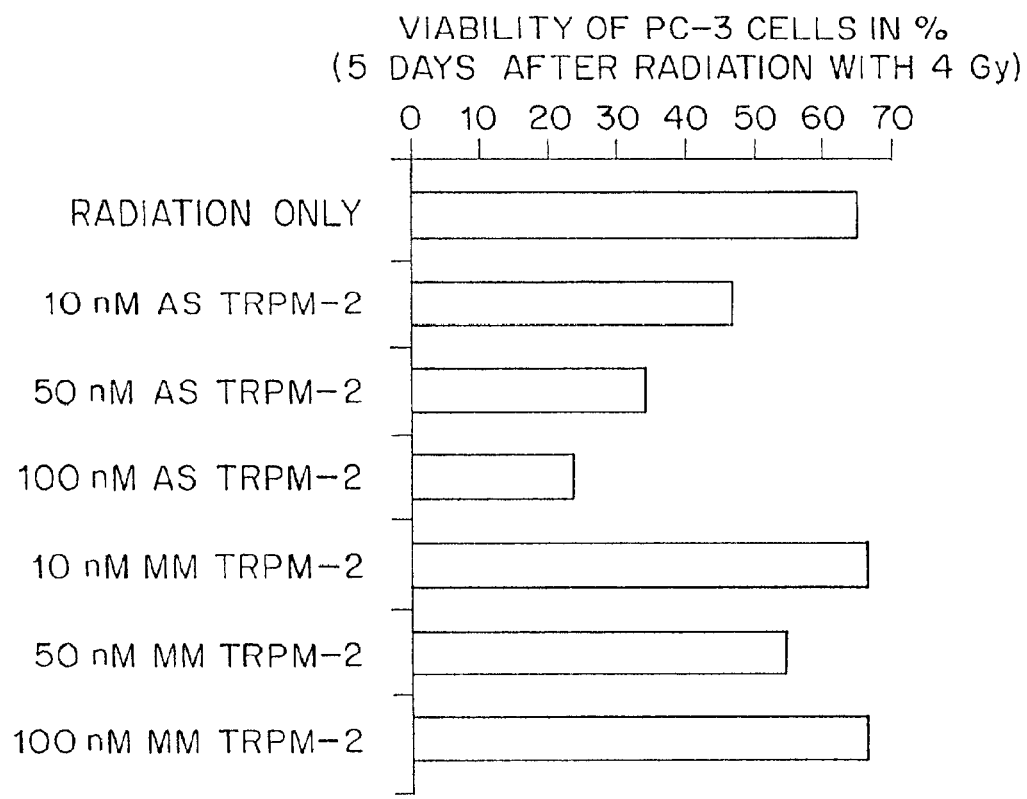
FIGS. 11A and 11B show the increased sensitivity of PC-3 cells to radiation after treatment with antisense TRPM-2 ODN.
Figure 11B:
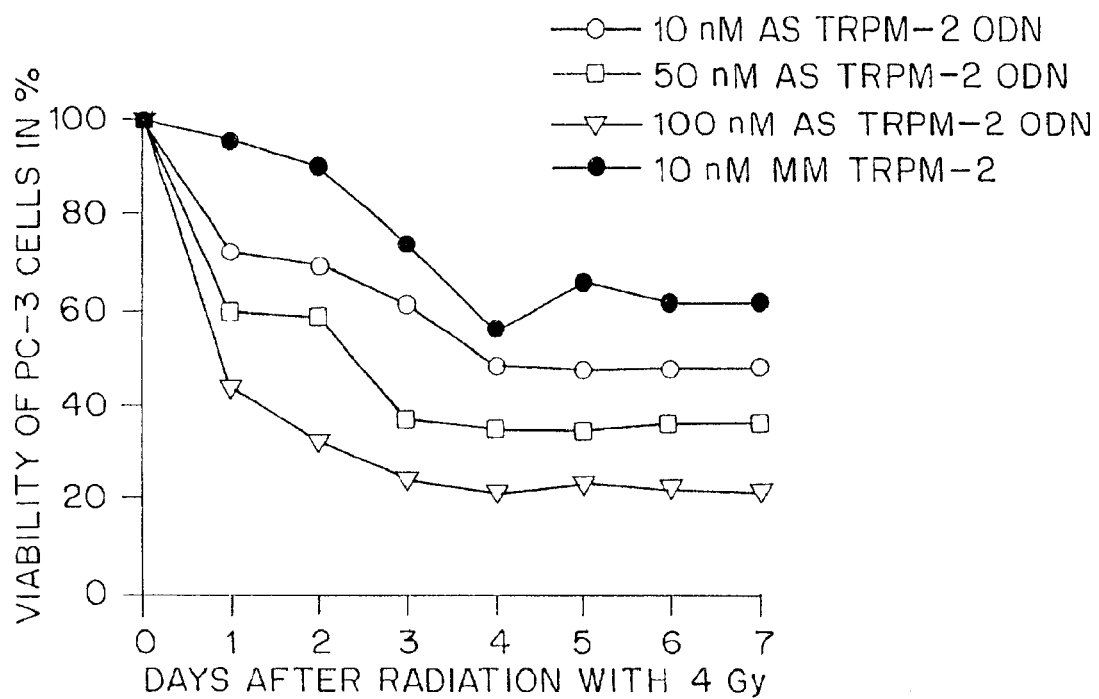

Antisense TRPM-2 ODNs enhance radiation sensitivity of cancer cells which express TRPM-2. Using northern analysis, we found that radiation therapy results in dose and time dependent increases in TRPM2 gene expression in human prostate cancer PC-3 cells (FIG. 8). Overexpression of TRPM2 results in increased resistance to radiation induced cell death. Human prostate LNCaP cells that overexpress TRPM2 (LNCaP/T1) are more resistant to radiation therapy (FIGS. 9A and B). Treatment of human prostate cancer PC-3 cells with 100 and 500 nM antisense TRPM-2 ODNs (Seq. ID. NO. 1) significantly reduces cell survival after a single treatment of 4 Gy radiation therapy compared to mismatch ODN (Seq. ID No. 2) treatment. (FIG. 10). FIGS. 11A and B show dose dependent radiation sensitization of human prostate cancer PC-3 cells after treatment with 10, 50, and 100 nM antisense TRPM-2 oligo in vitro.

EXAMPLE 8

To determine whether treatment with human antisense TRPM-2 ODN enhances chemosensitivity in the PC3 human prostate cancer cell line, mice bearing PC3 tumors were treated with antisense human TRPM-2 ODN plus micellar paclitaxel or mitoxantrone, and mismatch control ODN plus micellar paclitaxel or mitoxantrone (FIGS. 12A and 12B). ODN was administered for 28 days and either 0.5 mg micellar taxol or 0.3 mg mitoxantrone were administered on two occasions: from day 10 to 14, and day 24 to 28. A significant reduction in tumor size was observed in the antisense ODN treated animals as compared to those treated with mismatch control ODN. This effect was even more pronounced after the second dosing of the micellar paclitaxel or mitoxantrone.

EXAMPLE 9

Nucleoside Phosphoramidites for Oligonucleotide Synthesis

Deoxy and 2'-alkoxy amidites. 2'-Deoxy beta-cyanoethyldiisopropyl phosphoramidites were purchased from commercial sources (e.g. Chemgenes, Needham Mass. or Glen Research, Inc. Sterling Va.). Oligonucleotides containing 5-methyl-2'-deoxycytidine (5-Me-C) nucleotides were synthesized according to published methods (Sanghvi, et al., *Nucleic Acids Research* 21: 3197–3203 (1993)) using commercially available phosphoramidites (Glen Research, Sterling Va. or ChemGenes, Needham Mass.).

2'-O-(2-Methoxyethyl) modified amidites. 2'-O-Methoxyethyl-substituted nucleoside amidites are prepared as follows, or alternatively, as per the methods of Martin, P., *Helvetica Chimica Acta* 78: 486–504 (1995).

2,2'-Anhydro[1-(beta-D-arabinofuranosyl)-5-methyluridine]. 5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine. 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine. 2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g of additional product was obtained from the impure fractions to give a total yield of 183 g (57%).

3'-O-Acetyl-2'-O-methoxyethyl-5'-O-dimethoxytrityl-5-methyluridine. 2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane (4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine. A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine. A solution of 3'-O-acetyl-2'-O-methoxyethyl-5'-O-dimethoxytrityl-5-methyl-4-triazoleuridine (103 g, 0.141 dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine. 2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite. N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

EXAMPLE 10

Oligonucleotide synthesis. Phosphorothioate (P=S) oligonucleotides were synthesized on an automated DNA synthesizer (Applied Biosystems model 380B) using standard phosphoramidite chemistry except that iodine (for oxidation) was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and de-blocking in concentrated ammonium hydroxide at 55° C. (18 h), the oligonucleotides were purified by precipitating twice with 2.5 volumes of ethanol from a 0.5 M NaCl solution.

EXAMPLE 11

Synthesis of [2'-O-(2-Methoxyethyl)]—[2'-deoxy]—[2'-O-(Methoxyethyl)] Chimeric Phosphorothioate Oligonucleotides. Chimeric oligonucleotides having 2'-O-methoxyethyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-(methoxyethyl)-3'-O-phosphoramidite for 5' and 3' wings. The standard cycle is modified by increasing the wait step after the delivery of tetrazole and base to 600 s repeated four times for RNA and twice for 2'-O-methoxyethyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1 M TBAF in THF for 24 hrs at room temperature to deprotect the 2' positions. The reaction is then quenched with 1M TEAA and the sample is then reduced to ½ volume by rotovac before being desalted on a G25 size exclusion column. The oligonucleotide recovered is then analyzed spectrophotometrically for yield and for purity by capillary electrophoresis and by mass spectrometry.

[2'-O-(2-Methoxyethyl)Phosphodiester]—[2'-deoxy Phosphorothioate]—[2'-O-(2-2-Methoxyethyl) Phosphodiester] Chimeric Oligonucleotides. [2'-O-(2-methoxyethyl phosphodiester]—[2'-deoxy phosphorothioate]—[2'-O-(methoxyethyl) phosphodiester] chimeric oligonucleotides are prepared as per the above procedure, substituting oxidization with iodine to generate the phosphodiester internucleotide linkages within the wing portions of the chimeric structures and sulfurization (for example by 3,H-1,2 benzodithiole-3-one 1,1 dioxide (Beaucage Reagent)) to generate the phosphorothioate internucleotide linkages for the center gap.

EXAMPLE 12

Oligonucleotide Isolation. After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 266: 18162–18171 (1991). Results obtained with HPLC-purified material were similar to those obtained with non-HPLC purified material.

EXAMPLE 13

Northern analysis quantified changes in TRPM-2 mRNA levels in human PC-3 cells and tumors. The MTT assay measured effects of combined TRPM-2 antisense oligonucleotide plus paclitaxel on PC-3 cell growth. Athymic mice bearing PC-3 tumors were treated with paclitaxel plus either phosphorothioate antisense oligonucleotide, 2'-MOE antisense oligonucleotide, or mismatch control oligonucleotides for 28 days. Weekly body weights and serum-parameters were measured to assess toxicity. Tissue half-life of phosphorothioate and 2'-MOE antisense oligonucleotides in PC-3 tumors was assessed using capillary gel electrophoresis (CGE).

Tumor Cell Line. PC-3, derived from hormone-refractory human prostate cancer, was purchased from the American Type Culture Collection (Rockville, Md.). Cells were maintained in DMEM (Life Technologies, Inc., Gaithersburg, Md.), supplemented with 5% heat-inactivated fetal calf serum and routinely passaged when 90% confluent.

Antisense Oligonucleotides. Phosphorothioate and 2'-MOE antisense oligonucleotides used in this study were synthesized as described previously (Monia et al., *J Biol Chem* 268: 14514–14522 (1993); Dean et al., *J Biol Chem* 269: 16416–16424 (1994)). The sequence of the TRPM-2 antisense oligonucleotide used corresponded to the human TRPM-2 translation initiation site (5'-CAGCAGCAGAGTCTTCATCAT-3') (Seq. ID No. 4). A 2 base TRPM-2 mismatch oligonucleotide (5'-CAGCAGCAGAGT<u>A</u>TT<u>T</u>ATCAT-3') (Seq. ID No. 15) was used as a control. Conventional phosphorothioate antisense oligonucleotide was previously demonstrated to significantly inhibit TRPM-2 mRNA expression in a dose-dependent and sequence-specific manner (Miyake et al., *Clin. Cancer Res.*, 6: 1655–1666 (2000)). The sequence of the phosphorothioate and 2'-MOE antisense analogs, and their controls, were identical. The design of the 2'-MOE analogs was <u>CAG</u>CAGCAGAGTCTTCA<u>TCAT</u> in which the underlined bases represent 2'-MOE residues.

Treatment of Cells with Antisense Oligonucleotides. Lipofectin, a cationic lipid (Life Technologies, Inc.) was used to increase the antisense oligonucleotide uptake of cells. PC-3 cells were treated with various concentrations of antisense oligonucleotide after they had been pre-incubated for 20 min with 10 µg/ml lipofectin in serum free OPTI-MEM (Life Technologies, Inc.). Four hours after the beginning of the incubation, the medium containing antisense oligonucleotide and lipofectin was replaced with standard culture medium as described above.

Northern Blot Analysis. Total RNA was isolated from cultured PC-3 cells and PC-3 tumor tissues using the acid-guanidium thiocyanate-phenol-chloroform method. Electrophoresis, hybridization and washing conditions were carried out as previously reported in Miyake et al., *Oncogene* 16: 933–943 (1998). Human TRPM-2 and GAPDH cDNA probes were generated by reverse transcription-PCR from total RNA of human kidney using primers 5'-AAGGAAATTCAAAATGCTGTCAA-3' (sense) (Seq. ID No. 16) and 5'-ACAGACAAGATCTCCCGGCACTT-3' (antisense) (Seq. ID No. 17) for TRPM-2, and 5'-TGCTTTTAACTCTGGTAAAGT-3' (sense) (Seq. ID No. 18) and 5'-ATATTTGGCAGGTTTTTCTGA-3' (antisense) (Seq. ID No. 19) for GAPDH. Density of bands for TRPM-2 was normalized against that of GAPDH by densitometric analysis.

Capillary Gel Electrophoresis (CGE). CGE (PACE 5000 System, Beckman, Fullerton, Calif.) was used to determine the fraction of full-length antisense oligonucleotide in PC-3 tumors and confirmed by 20% denaturing PAGE and laser scanning densitometry (Molecular Dynamics, Sunnyvale, Calif.). For CGE, a 100 µl solution of antisense oligonucleotide, at a concentration of ~0.1 $AU_{260}$, was utilized for electrokinetic injection at −5 kV into a 45 cm polyacrylamide-filled capillary column utilizing a 100 mM tris-borate (pH=8.0) running buffer. Separation was performed at −10 kV over 30 minutes with peak detection measured via UV absorption at 260 nM.

MTT Assay. The in vitro growth inhibitory effects of conventional phosphorothioate antisense oligonucleotide plus paclitaxel or docetaxel versus 2'-MOE antisense oligonucleotide plus paclitaxel or docetaxel on PC-3 cells were compared using the MTT assay as previously described (Miyake et al., *Oncogene* 16: 933–943 (1998)). Briefly, $1\times10^4$ cells were seeded in each well of 96-well microtiter plates and allowed to attach overnight. Cells were then treated once daily with 500 nM of either TRPM-2 antisense oligonucleotide or mismatch control oligonucleotides for 2 days. Following antisense oligonucleotide treatment, cells were treated with various concentrations of paclitaxel or docetaxel. After 48 h of incubation, 20 µl of 5 mg/ml MTT (Sigma Chemical Co.) in PBS was added to each well, followed by incubation for 4 h at 37° C. The formazan crystals were dissolved in dimethyl sulfoxide (DMSO). The optical density was determined with a microculture plate reader (Becton Dickinson Labware, Lincoln Park, N.J.) at 540 nm. Absorbance values were normalized to the values obtained for the vehicle-treated cells to determine the percentage of survival. Each assay was performed in triplicate.

In Vivo Treatments. Approximately 1×10$^6$ human PC-3 cells were inoculated s.c. with 0.1 ml of Matrigel (Becton Dickinson Labware, Bedford, Mass.) on the flank of 6 to 8 week old male athymic mice under halothane anaesthesia (5% induction- and 1.5% maintenance-concentration). When PC-3 tumors grew to 10 mm in diameter, usually 4–6 weeks after injection, treatment of the animals was started.

In a first experiment, mice were randomized to one of 3 arms for treatment with conventional phosphorothioate antisense oligonucleotide plus paclitaxel, 2'-MOE antisense oligonucleotide plus paclitaxel, or phosphorothioate mismatch control oligonucleotides plus paclitaxel. Each experimental group consisted of 10 mice. After randomization, 12.5 mg/kg of either type of TRPM-2 antisense oligonucleotide or mismatch control oligonucleotides were injected i.p. once daily into each mouse for 28 days. From days 10 to 14, and from days 24 to 28, 0.5 mg polymeric micellar paclitaxel was administered once daily by i.v. injection according to the method in Leung et al., *Prostate* 44: 156–163 (2000). Tumor volume was measured once weekly and calculated by the formula: length×width×depth×0.5236. Data points were reported as mean tumor volumes±standard deviation. In each of the 3 treatment arms, 3 mice were designated immediately after randomization to be harvested 1 week after the last oligonucleotide/paclitaxel treatment (day 35) to determine multiple serum-parameters for comparison of in vivo antisense oligonucleotide toxicity.

In a second set of experiments, mice were randomized to one of 4 arms for treatment with phosphorothioate antisense oligonucleotide once daily, phosphorothioate antisense oligonucleotide once weekly, 2'-MOE antisense oligonucleotide once weekly, or phosphorothioate mismatch control oligonucleotides once weekly. Each experimental group consisted of 8 mice. After randomization, 12.5 mg/kg TRPM-2 antisense oligonucleotide or mismatch control oligonucleotides were injected i.p. once daily or once weekly into each mouse over 4 weeks. Animals in all 4 treatment arms additionally received polymeric micellar paclitaxel as described above. Tumor volume was measured and data points were reported as described above.

In a third in vivo experiment, mice were randomized to one of 2 arms for treatment with either phosphorothioate antisense oligonucleotide or 2'-MOE antisense oligonucleotide. Each experimental group consisted of 12 mice. 12.5 mg/kg TRPM-2 antisense oligonucleotide was injected i.p. once daily into each mouse for 5 days. PC-3 tumors were harvested 1, 3, 5, and 7 days after the last antisense oligonucleotide injection for Northern blot and CGE-analysis of TRPM-2. All animal procedures were performed according to the guidelines of the Canadian Council on Animal Care and with appropriate institutional certification.

Enhanced Inhibition of TRPM-2 mRNA Using 2'-MOE Modified Antisense Oligonucleotide in PC-3 cells. Northern blot analysis was used to compare the effects of treatment with conventional phosphorothioate antisense oligonucleotide and 2'-MOE antisense oligonucleotide on TRPM-2 mRNA expression in PC-3 cells. Both phosphorothioate antisense oligonucleotide and 2'-MOE antisense oligonucleotide decreased TRPM-2 mRNA levels in a dose-dependent and sequence-specific manner. Using an antisense oligonucleotide concentration of 500 nM, 2'-MOE antisense oligonucleotide was more potent than conventional phosphorothioate antisense oligonucleotide, decreasing TRPM-2 mRNA levels in PC-3 cells by 80% versus 40%.

Conventional Phosphorothioate and 2'-MOE Modified TRPM-2 Antisense Oligonucleotide Equally Enhance Chemosensitivity of PC-3 Cells in Vitro. To compare the efficacy of conventional phosphorothioate antisense oligonucleotide and 2'-MOE antisense oligonucleotide to enhance cytotoxicity in vitro, PC-3 cells were treated with either type of TRPM-2 antisense oligonucleotide once daily for 2 days and then incubated with medium containing various concentrations of either paclitaxel or docetaxel. After 48 h of incubation, cell viability was determined by the MTT assay. The result was that both types of TRPM-2 antisense oligonucleotide equally enhanced chemo-sensitivity of paclitaxel and docetaxel by more than 70% and 50%, respectively.

Enhanced Tissue Half-Life of Antisense Oligonucleotide by 2'-MOE Modification. CGE was used to analyze time-dependent antisense oligonucleotide metabolism in PC-3 tumors. In vivo tissue half-life of antisense oligonucleotide was increased by more than 5-fold with the 2'-MOE modification, compared to conventional phosphorothioate antisense oligonucleotide (>5 days versus <1 day). 90% of 2'-MOE antisense oligonucleotide was detectable as full length material at 1 week, whereas only 10% of phosphorothioate antisense oligonucleotide was found as full-length material at 1 day following cessation of dosing. Five and 7 days following the last antisense oligonucleotide treatment, no full length phosphorothioate antisense oligonucleotide was detectable in tumor tissue. Furthermore, in vivo TRPM-2 mRNA expression was more efficiently inhibited over this time period using 2'-MOE antisense oligonucleotide compared to phosphorothioate antisense oligonucleotide.

2'-MOE Modified TRPM-2 Antisense Oligonucleotide Enhances the Potency of Paclitaxel In Vivo. To compare the efficacy of conventional phosphorothioate antisense oligonucleotide versus 2'-MOE antisense oligonucleotide to enhance the cytotoxicity of paclitaxel in vivo, athymic mice bearing PC-3 tumors were treated with either type of TRPM-2 antisense oligonucleotide or mismatch control oligonucleotide over 28 days. From days 10 to 14, and from days 24 to 28, 0.5 mg polymeric micellar paclitaxel was administered once daily by i.v. injection. Both types of TRPM-2 antisense oligonucleotides enhanced paclitaxel chemosensitivity in PC-3 tumors by 7 weeks following initiation of treatment. Treatment with 2'-MOE antisense oligonucleotide was significantly more potent in reducing mean tumor volume (over 80%) than conventional phosphorothioate antisense oligonucleotide (40%), as compared to treatment with mismatch control oligonucleotides. No side effects were observed for either compound.

Weekly Administration of 2'-MOE Modified TRPM-2 Antisense Oligonucleotide is Equivalent to Daily Administration of Conventional Phosphorothioate TRPM-2 Antisense Oligonucleotide In Vivo. To assess whether increased stability and longer tissue half-life of 2'-MOE antisense oligonucleotide would permit longer dosing intervals without loss of efficiency, athymic mice bearing PC-3 tumors were treated with either type of TRPM-2 antisense oligonucleotide or mismatch control oligonucleotides once weekly compared to conventional phosphorothioate antisense oligonucleotide once daily. From days 10 to 14, and from days 24 to 28, 0.5 mg polymeric micellar paclitaxel was administered once daily by i.v. injection. In combination with paclitaxel, weekly administration of 2'-MOE antisense oligonucleotide was equivalent to daily administration of conventional phosphorothioate antisense oligonucleotide, reducing mean tumor volumes by 31% compared to weekly administration of mismatch control oligonucleotides and by 21% compared to weekly administration of conventional phosphorothioate antisense oligonucleotide, following 6 weeks after initiation of treatment.

What is claimed is:

1. A compound consisting of an oligonucleotide of sequence CAGCAGCAGAGTCTTCATCAT; SEQ ID NO: 4, wherein the oligonucleotide has a phosphorothioate backbone throughout, the sugar moieties of nucleotides 1–4 and 18–21 bear 2'-O-methoxyethyl modifications, and the remaining nucleotides (nucleotides 5–17) are 2'-deoxynucleotides, and wherein the cytosines of nucleotides 1, 4 and 19 are 5-methylcytosines.

2. A method for delaying progression of prostatic tumor cells to an androgen-independent state, comprising treating androgen-sensitive prostatic tumor cells in vivo with an antisense oligonucleotide which inhibits expression of TRPM-2 by the tumor cells, wherein the antisense oligonucleotide has the sequence given by SEQ ID No. 4, wherein the oligonucleotide has a phosphorothioate backbone throughout, the sugar moieties of nucleotides 1–4 and 18–21 bear 2'-O-methoxyethyl modifications, and the remaining nucleotides (nucleotides 5–17) are 2'-deoxynucleotides, and wherein the cytosines of nucleotides 1, 4 and 19 are 5-methylcytosines.

3. A method for treating prostate cancer in an individual suffering from prostate cancer, comprising the steps of initiating androgen-withdrawal to induce apoptotic cell death of prostatic tumor cells in the individual, and administering to the individual a composition effective to inhibit expression of TRPM-2 by the tumor cells, thereby delaying the progression of prostatic tumor cells to an androgen-independent state in an individual, wherein the composition effective to inhibit expression of TRPM-2 is an antisense oligonucleotide, wherein the antisense oligonucleotide has the sequence given by SEQ ID No. 4, wherein the oligonucleotide has a phosphorothioate backbone throughout, the sugar moieties of nucleotides 1–4 and 18–21 bear 2'-O-methoxyethyl modifications, and the remaining nucleotides (nucleotides 5–17) are 2'-deoxynucleotides, and wherein the cytosines of nucleotides 1, 4 and 19 are 5-methylcytosines.

4. The method of claim 3, further comprising the step of administering to the individual a chemotherapy agent.

5. The method of claim 4, wherein the chemotherapy agent is a taxane or mitoxanthrone.

6. The method of claim 3, further comprising the step of administering to the individual a second antisense oligonucleotide which inhibits expression of an anti-apoptotic protein other than TRPM-2.

7. The method of claim 6, wherein the second antisense oligonucleotide is antisense Bcl-2 oligonucleotide.

8. The method of claim 6, further comprising the step of administering to the individual a chemotherapy agent.

9. The method of claim 8, wherein the chemotherapy agent is a taxane or mitoxanthrone.

10. A method for enhancing the chemo- or radiation sensitivity of cancer cells in an individual suffering from a cancer that expresses TRPM-2 in amounts different from normal tissue of the same type, comprising administering to the individual a composition effective to inhibit expression of TRPM-2 by cancer cells, wherein the composition effective to inhibit expression of TRPM-2 is an antisense oligonucleotide, wherein the antisense oligonucleotide has the sequence given by SEQ ID No. 4, wherein the oligonucleotide has a phosphorothioate backbone throughout, the sugar moieties of nucleotides 1–4 and 18–21 bear 2'-O-methoxyethyl modifications, and the remaining nucleotides (nucleotides 5–17) are 2'-deoxynucleotides, and wherein the cytosines of nucleotides 1, 4 and 19 are 5-methylcytosines.

11. A method of delaying of progression of a population of prostatic tumor cells from a state in which living prostatic tumor cells are androgen-sensitive to a state in which living tumor cells are androgen independent, comprising treating the population of androgen-sensitive prostatic tumor cells with an antisense oligonucleotide which inhibits expression of TRPM-2 by the tumor cells, wherein the antisense oligonucleotide has the sequence given by SEQ ID No. 4, wherein the oligonucleotide has a phosphorothioate backbone throughout, the sugar moieties of nucleotides 1–4 and 18–21 bear 2'-O-methoxyethyl modifications, and the remaining nucleotides (nucleotides 5–17) are 2'-deoxynucleotides, and wherein the cytosines of nucleotides 1, 4 and 19 are 5-methylcytosines.

* * * * *